US006306423B1

(12) United States Patent
Donovan et al.

(10) Patent No.: US 6,306,423 B1
(45) Date of Patent: Oct. 23, 2001

(54) NEUROTOXIN IMPLANT

(75) Inventors: Stephen Donovan, Capistrano Beach; Daniel G. Brady, San Juan Capistrano, both of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/587,250

(22) Filed: Jun. 2, 2000

(51) Int. Cl.$^7$ .............................. A61F 2/00; A61F 13/00; A61K 9/14; A61K 39/02; A61K 39/08

(52) U.S. Cl. ........................ 424/423; 424/422; 424/484; 424/486; 424/236.1; 424/247.1; 514/964

(58) Field of Search .................................. 424/423, 422, 424/426, 184.1, 204.1, 206.1, 234, 236.1, 244, 247.1, 259, 260, 274.1; 514/964

(56) References Cited

U.S. PATENT DOCUMENTS

| | | |
|---|---|---|
| 3,523,906 | 8/1970 | Vrancken et al. . |
| 3,691,909 | 9/1972 | Kitajima et al. . |
| 3,737,337 | 6/1973 | Schnoring et al. . |
| 4,389,330 | 6/1983 | Tice et al. . |
| 4,474,572 | 10/1984 | McNaughton et al. . |
| 5,019,400 | 5/1991 | Gombotz et al. . |
| 5,183,462 | 2/1993 | Borodic . |
| 5,298,019 | 3/1994 | Borodic . |
| 5,401,243 | 3/1995 | Borodic . |
| 5,667,808 | 9/1997 | Johnson et al. . |
| 5,906,826 * | 5/1999 | Emery et al. ........................ 424/422 |
| 5,980,945 | 11/1999 | Ruiz . |
| 5,989,545 | 11/1999 | Foster et al. . |
| 6,001,386 | 12/1999 | Ashton et al. . |
| 6,007,843 | 12/1999 | Drizen et al. . |
| 6,011,011 | 1/2000 | Hageman . |
| 6,022,554 | 2/2000 | Lee et al. . |

FOREIGN PATENT DOCUMENTS

| | | |
|---|---|---|
| 94/15629 * | 7/1994 | (WO) . |
| WO 94/15629 | 7/1994 | (WO) . |

OTHER PUBLICATIONS am Ende, M.T., et al.; Factors Influencing Drug and Protein transport and Release from Ionic Hydrogels; *Reactive Polymers;* 25:127–137 (1995).

Aoki, K.R.; Preclinical Update on BOTOX® (Botulinum Toxin Type A)–Purified Neurotoxin Complex Relative to other Botulinum Neurotoxin Preparations; *European Journal of Neurology;* 6(Suppl 4):S3–S10 (1999).

Bell, C.L., et al.; Poly(Methacrylic Acid–g–Ethylene Glycol) Hydrogels as pH Responsive Biomedical Materials; Mat. Res. Soc. Symp. Proc.; 331:199–204 (1994).

Bigalke, H., et al.; Botulinum A Neurotoxin Inhibits Non–Cholinergic Synaptic Transmission in Mouse Spinal Cord Neurons in Culture; *Brain Research,* 360:318–324 (1985).

Bigalke, H., et al.; Tetanus Toxin and Botulinum A. Toxin Inhibit Release and Uptake of Various Transmitters, as Studied with Particulate Preparations from Rat Brain and Spinal Cord; *Naunyn–Schmiedeberg's Arch. Pharmacol;* 316:244–251 (1981).

Boyd, R.S., et al.; The Effect of Botulinum Neurotoxin–B on Insulin Release from a B–Cell Line; *Movement Disorders;* 10(3), Item 19; 376 (1995).

Boyd, R.S., et al.; The Insulin Secreting B–Cell Line HIT–15 Contains SNAP–25 Which is a Target for Botulinum Neurotoxin–A; *Movement Disorders;* 10(3), Item 20; 376 (1995).

Brazel, C.S., et al.; Temperature– and pH–Sensitive Hydrogels for Controlled Release of Antithrombotic Agents; Mat. Res. Soc. Symp. Proc.; 331:211–216 (1994).

Cardamone, M., et al.; In Vitro Testing of a Pulsatile Delivery System and its In Vivo Application for Immunisation Against Tetanus Toxoid; *Journal of Controlled Release;* 47:205–219 (1997).

Cleland, J.L., et al.; Development of a Single–Shot Subunit Vaccine for HIV–1. 5. Programmable in Vivo Autoboost and Long Lasting Neutralizing Response; *Journal of Pharmaceutical Sciences;* vol. 87, No. 12; p. 1489–1495 (Dec. 1998).

Cleland, J.L.; Solvent Evaporation Processes for the Production of Controlled Release Biodegradable Microsphere Formulations for Therapeutics and Vaccines; *Biotechnol. Prog.;* 14:102–107 (1998).

Curley, J., et al.; Prolonged Regional Nerve Blockade— Injectable Biodegradable Bupivacaine/Polyester Microspheres; *Anesthesiology;* vol. 84(6):1401–1410 (Jun. 1996).

(List continued on next page.)

Primary Examiner—Thurman K. Page
Assistant Examiner—Blessing Fubara
(74) *Attorney, Agent, or Firm*—Martin A. Voet; Robert J. Baran; Carlos A. Fisher

(57) ABSTRACT

A biocompatible implant for continuous in vivo release of a neurotoxin over a treatment period extending from one month to five years. The implant can be made of casting a solution of a polymer, such as an ethyl vinyl acetate copolymer and the neurotoxin. The neurotoxin can be a botulinum toxin.

20 Claims, No Drawings

OTHER PUBLICATIONS

Darney, P.D.; Hormonal Implants: Contraception for a New Century; *Am. J. Obstet. Gynecol.;* 170(5)(2):1536–1543 (May 1994).

Doelker, E.; Cellulose Derivatives; *Advances in Polymer Science;* 107:199–265 (1993).

Dong, L.C., et al., A Novel Approach for Preparation of pH–Sensitive Hydrogels for Enteric Drug Delivery; *Journal of Controlled Release;* 15:141–152 (1991).

Elan Corporation press release; Elan to Acquire the Liposome Company—A Step in the Building of an Oncology Presence; 2 pages (Mar. 6, 2000).

Fauci, A.S., et al. (Editors); *Harrison's Principles of Internal Medicine,* 14$^{th}$ Edition; McGraw–Hill (1998).

Fung, L.K., et al; Pharmacokinetics of Interstitial Delivery of Carmustine, 4–Hydroperoxycyclophosphamide, and Paclitaxel from a Biodegradable Polymer Implant in the Monkey Brain; *Cancer Research;* 58:672–684 (Feb. 15, 1998).

Garry, M.G., et al.; Evaluation of the Efficacy of a Bioerodible Bupivacaine Polymer System on Antinociception and Inflammatory Mediator Release; *Pain;* 82:49–55 (1999).

Gonelle–Gispert, C., et al.; SNAP–25A And–25B Isoforms are Both Expressed in Insulin–Secreting Cells and Can Function in Insulin Secretion; *Biochem. J.;* 339:159–165 (1999).

Habermann, E., et al.; Tetanus Toxin and Botulinum A and C Neurotoxins Inhibit Noradrenaline Release from Cultured Mouse Brain; *Journal of Neurochemistry;* vol. 51(2); 522–527 (1988).

Habermann, E.; Inhibition by Tetanus and Botulinum A Toxin of the Release of ($^3$H)noradrenaline and ($^3$H)GABA from Rat Brain Homogenate; *Experientia* 44:224–226 (1988).

Habermann, E.; I–Labeled Neurotoxin from *Clostridium Botulinum* A: Preparation, Binding to Synaptosomes and Ascent to the Spinal Cord; *Naunyn–Schmiedeberg's Arch. Pharmacol.;* 281, 47–56 (1974).

Haller, M.F., et al., Localized Delivery of Proteins in the Brain: Can Transport be Customized?; *Pharmaceutical Research;* 15(3):377–385 (1998).

Hanes, J., et al.; New Advances in Microsphere–Based Single–Dose Vaccines; *Advanced Drug Delivery Reviews;* 28:97–119 (1997).

Jankovic, J., et al.; *Therapy with Botulinum Toxin;* Marcel Dekker, Inc., publisher; p. 5 (1994).

Jeong, B., et al.; Biodegradable Block Copolymers as Injectable Drug–Delivery Systems; *Nature,* 388:860–862 (Aug. 28, 1997).

Jeyanthi, R., et al.; Collagen–Poly(HEMA) Hydrogels for the Controlled Release of Anticancer Drugs—Preparation and Characterization; *Journal of Bioactive and Compatible Polymers;* 5:194–211 (Apr. 1990).

Johansen, P., et al.; Improving Stability and Release Kinetics of Microencapsulated Tetanus Toxoid by Co–Encapsulation of Additives; *Pharmaceutical Research;* 15(7):1103–1110 (1998).

Kissel, T., et al.; B. Various Delivery Systems; *Behring Inst. Mitt.;* 98:172–183 (1997).

Kost, J., et al.; Magnetically Enhanced Insulin Release in Diabetic Rats; *Journal of Biomedical Materials Research;* 21:1367–1373 (1987).

Krewson, C.E., et al.; Distribution of Nerve Growth Factor Following Direct Delivery to Brain Interstitium; *Brain Research;* 680:196–206 (1995).

Krewson, C.E., et al.; Transport and Elimination of Recombinant Human NGF During Long–Term Delivery to the Brain; *Brain Research;* 727:169–181 (1996).

Krewson, C.E., et al.; Stabilization of Nerve Growth Factor in Controlled Release Polymers and in Tissue; *J. Biomater. Sci. Polymer Edn.;* 8(2):103–117 (1996).

Langer, R., New Methods of Drug Delivery; *Science,* 249:1527–1533 (Sep. 28, 1990).

Langer, R., et al.; Polymers for the Sustained Release of Proteins and Other Macromolecules; *Nature,* 263:797–800 (Oct. 28, 1976).

Laskawi, R., et al.; Up–to–Date Report of Botulinum Toxin Type A Treatment in Patients with Gustatory Sweating (Frey's Syndrome); *Laryngoscope;* 108:381–384 (Mar. 1998).

Luo, D., et al.; Controlled DNA Delivery Systems; *Pharmaceutical Research;* 16(8):1300–1308 (1999).

Mahoney, M.J., et al., Millimeter–Scale Positioning of a Nerve–Growth–Factor Source and Biological Activity in the Brain; *Proc. Natl. Acad. Sci. USA;* 96:4536–4539 (Apr. 1999).

Mak, M., et al.; Distribution of Drugs Following Controlled Delivery to the Brain Interstitium; *Journal of Neuro–Oncology;* 26:91–102 (1995).

Masters, D.B., et al.; Prolonged Regional Nerve Blockade by Controlled Release of Local Anesthetic from a Biodegradable Polymer Matrix; *Anesthesiology;* 79:340–346 (1993).

Masters, D.B., et al.; Sustained Local Anesthetic Release from Bioerodible Polymer Matrices: A Potential Method for Prolonged Regional Anesthesia; *Pharmaceutical Research;* 10(10):1527–1532 (1993).

Naumann, M., et al.; Botulinum Toxin Type A in the Treatment of Focal, Axillary and Palmar Hyperhidrosis and Other Hyperhidrotic Conditions; *European Journal of Neurology;* vol. 6(suppl4) S111–S115 (1999).

Pearce, L. B., et al.; Pharmacologic Characterization of Botulinum Toxin for Basic Science and Medicine; *Toxicon;* vol. 35(9); 1373–1412 (1997).

Peralta, O., et al.; Subdermal Contraceptive Implants; *J. Steroid Biochem. Molec. Biol.;* 53(1–6): 223–226 (1995).

Powell, E.M., et al.; Controlled Release of Nerve Growth Factor from a Polymeric Implant; *Brain Research;* 115:309–311 (1990).

Ragona, R.M., et al.; Management of Parotid Sialocele with Botulinum Toxin; *The Laryngoscope;* 109:1344–1346 (Aug. 1999).

Rao, J.K., et al., Implantable Controlled Delivery Systems for Proteins Based on Collagen—pHEMA Hydrogels; *Biomaterials;* 15(5): 383–389 (1994).

Saltzman, W.M. et al.; Transport Rates of Proteins in Porous Materials with Known Microgeometry; *Biophys. J.;* 55:163–171; (Jan. 1989).

Saltzman, W.M., et al., Intracranial Delivery of Recombinant Nerve Growth Factor: Release Kinetics and Protein Distribution from Three Delivery Systems; *Pharmaceutical Research;* 16(2):232–240 (1999).

Sanchez–Prieto, J., et al.; Botulinum Toxin A Blocks Glutamate Exocytosis from Guinea–Pig Cerebral Cortical Synaptosomes; *Eur. J.Biochem.;* 165:675–681 (1987).

Schantz, E.J., et al., Properties and Use of Botulinum Toxin and Other Microbial Neurotoxins in Medicine; *Microbiol Rev.*, 56:80–99 (1992).

Singh, B.R.; Critical Aspects of Bacterial Protein Toxins; *Natural Toxins II;* Plenum Press, New York; pp. 63–84 (1996).

Sinha, V.R., et al.; Bioabsorbable Polymers for Implantable Therapeutic Systems; *Drug Development and Industrial Pharmacy;* 24(12):1129–1138 (1998).

Sloop, R.R., et al.; Reconstituted Botulinum Toxin Type A Does Not Lose Potency in Humans if it is Refrozen or Refrigerated for 2 Weeks Before Use; *Neurology;* 48:249–253 (Jan. 1997).

Strasser, J.F., et al.; Distribution of 1,3–bis(2–Chloroethyl)–1–Nitrosourea and Tracers in the Rabbit Brain After Interstitial Delivery by Biodegradable Polymer Implants; *The Journal of Pharmacology and Experimental Therapeutics;* 275(3):1647–1655 (1995).

Tobio, M., et al.; A Novel System Based on a Poloxamer/PLGA Blend as a Tetanus Toxoid Delivery Vehicle; *Pharmaceutical Research;* 16(5):682–688 (1999).

Veronese, F.M., et al.; Polyorganophosphazene Microspheres for Drug Release: Polymer Synthesis, Microsphere Preparation, in vitro and in vivo Naproxen Release; *Journal of Controlled Release;* 52:227–237 (1998).

Von Recum, A.F., et al., Editor; *Handbook of Biomaterials Evaluation—Scientific, Technical, and Clinical Testing of Implant Materials;* $2^{nd}$ Edition; Taylor & Francis; p. 30–33 (1998).

Weigand, H., et al.; I–Labelled Botulinum A Neurotoxin: Pharmacokinetics in Cats After Intramuscular Injection; *Naunyn–Schmiedeberg's Arch. Pharmacol.;* 292:161–165 (1976).

Winn, S.R., et al.; Polymer–Encapsulated Genetically Modified Cells Continue to Secrete Human Nerve Growth Factor for over One Year in Rat Ventricles: Behavioral and Anatomical Consequences; *Experimental Neurology;* 140:126–138 (1996).

* cited by examiner

NEUROTOXIN IMPLANT

BACKGROUND

The present invention relates to a controlled release drug delivery system. In particular, the present invention relates to a controlled release neurotoxin delivery system.

A controlled release system can deliver a drug in vivo at a predetermined rate over a specific time period. Generally, release rates are determined by the design of the system, and can be largely independent of environmental conditions such as pH. Controlled release systems which can deliver a drug over a period of several years are known. Contrarily, sustained release systems typically deliver drug in 24 hours or less and environmental factors can influence the release rate. Thus, the release rate of a drug from an implanted controlled release system (an "implant") is a function of the physiochemical properties of the carrier implant material and of the drug itself. Typically, the implant is made of an inert material which elicits little or no host response.

A controlled release system can be comprised of a drug with a biological activity incorporated into a carrier. The carrier can be a polymer or a bioceramic material. The controlled release system can be injected, inserted or implanted into a selected location of a patient's body and reside therein for a prolonged period during which the drug is released by the implant in a manner and at a concentration which provides a desired therapeutic efficacy.

Polymeric materials can release drugs due to diffusion, chemical reaction or solvent activation, as well as upon influence by magnetic, ultrasound or temperature change factors. Diffusion can be from a reservoir or matrix. Chemical control can be due to polymer degradation or cleavage of the drug from the polymer. Solvent activation can involve swelling of the polymer or an osmotic effect. See e.g. Science 249;1527–1533:1990.

A membrane or reservoir implant depends upon the diffusion of a bioactive agent across a polymer membrane. A matrix implant is comprised of a polymeric matrix in which the bioactive agent is uniformly distributed. Swelling-controlled release systems are usually based on hydrophilic, glassy polymers which undergo swelling in the presence of biological fluids or in the presence of certain environmental stimuli.

Preferably, the implant material used is substantially non-toxic, non-carcinogenic, and non-immunogenic. Suitable implant materials include polymers, such as poly(2-hydroxy ethyl methacrylate) (p-HEMA), poly(N-vinyl pyrrolidone) (p-NVP)+, poly(vinyl alcohol) (PVA), poly (acrylic acid) (PAA), polydimethyl siloxanes (PDMS), ethylene-vinyl acetate (EVAC) copolymers, polyvinylpyrrolidone/methylacrylate copolymers, polymethylmethacrylate (PMMA), poly(lactic acid) (PLA), poly (glycolic acid) (PGA), polyanhydrides, poly(ortho esters), collagen and cellulosic derivatives and bioceramics, such as hydroxyapatite (HPA), tricalcium phosphate (TCP), and aliminocalcium phosphate (ALCAP). Lactic acid, glycolic acid and collagen can be used to make biodegradable implants.

Controlled release systems comprising a polymer for prolonged delivery of a therapeutic drug are known. For example, a subdermal reservoir implant comprised of a nonbiodegradable polymer can be used to release a contraceptive steroid, such as progestin, in amounts of 25–30 mg/day for up to sixty months (i.e. the Norplant® implant). Additionally, Dextran (molecular weight about 2 million) has been released from implant polymers.

An implant material can be biodegradable or bioerodible. An advantage of a bioerodible implant is that is does not need to be removed from the patient. A bioerodible implant can be based upon either a membrane or matrix release of the bioactive substance. Biodegradable microspheres prepared from PLA-PGA are known for subcutaneous or intramuscular administration.

A degradable implant preferably retains its structural integrity throughout its duration of controlled release so that it can be removed if removal is desired or warranted. After the incorporated drug falls below a therapeutic level, a biodegradable implant can degrade completely without retaining any drug which can be released at low levels over a further period. Subdermal implants and injectable microspheres made of degradable materials, such as lactic acid-glycolic acid copolymers, polycaprolactones and cholesterol, for steroid delivery, are known.

Protein Implants

Controlled release systems for large macromolecules, such as proteins are known. Thus, biocompatible, polymeric pellets which incorporate a high molecular weight protein have been implanted and shown to exhibit continuous release of the protein for periods exceeding 100 days. Various labile, high molecular weight enzymes (such as alkaline phosphatase, molecular weight 88 kD and catalase, molecular weight 250 kD) have been incorporated into biocompatible, polymeric implants with long term, continuous release characteristics. Generally an increase in the polymer concentration in the casting solution decreases the initial rate at which protein is released from the implant. Nature 263; 797–800:1976.

Additionally, albumin can be released from an EVAc implant and polylysine can be released from collagen based microspheres. Mallapragada S. K. et al, at page 431 of chapter 27 in Von Recum, A. F. Handbook of Biomaterials Evaluation, second edition, Taylor & Francis (1999). Additionally, the release of tetanus toxoid from microspheres has been studied. Ibid at 432. Sintered EVAc copolymer inserted subcutaneously has been shown to release insulin over a period of 100 days. Ibid at 433.

Furthermore, it is known to encapsulate a protein, such as human growth hormone (hGH) (molecular weight about 26 kD), within a polymeric matrix which when implanted permits the human growth hormone to be released in vivo over a period of about a week. U.S. Pat. No. 5,667,808.

A controlled release system (i.e. an "implant") can exhibit a high initial burst of protein release, followed by minimal release thereafter. Unfortunately, due to the high concentration of protein within a controlled release matrix, the protein molecules tend to aggregate and form denatured, immunogenic concentrations of protein.

Pulsatile Release Implants

Hydrogels have been used to construct single pulse and multiple pulse drug delivery implants. A single pulse implant can be osmotically controlled or melting controlled. Doelker E., Cellulose Derivatives, Adv Polym Sci 107; 199–265:1993. It is known that multiple pulses of certain substances from an implant can be achieved in response to an environmental change in a parameter such as temperature (Mater Res Soc Symp Proc, 331;211–216:1994; J. Contr Rel 15;141–152:1991), pH (Mater Res Soc Symp Proc, 331;199–204:1994), ionic strength (React Polym, 25;127–137:1995), magnetic fields (J. Biomed Mater Res, 21;1367–1373:1987) or ultrasound.

Unfortunately, a subcutaneous implantable drug pellet made of a nonbiodegradable polymer has the drawback of requiring both surgical implantation and removal. Use of a biocompatible, bioerodible implant can overcome the evident deficiencies of nonbiodegradable implants. A biodegradable implant can release a drug over a long period of time with simultaneous or subsequent degradation of the polymer within the tissue into constituents, thereby avoiding any need to remove the implant. See e.g. *Drug Development and Industrial Pharmacy* 24(12);1129–1138:1998.

A degradable polymer can be a surface eroding polymer, as opposed to a polymer which displays bulk or homogenous. A surface eroding polymer degrades only from its exterior surface, and drug release is therefore proportional to the polymer erosion rate. A suitable such polymer can be a polyanhydride.

Botulinum Toxin

The anaerobic, gram positive bacterium Clostridium botulinum produces a potent polypeptide neurotoxin, botulinum toxin, which causes a neuroparalytic illness in humans and animals referred to as botulism. The spores of Clostridium botulinum are found in soil and can grow in improperly sterilized and sealed food containers of home based canneries, which are the cause of many of the cases of botulism. The effects of botulism typically appear 18 to 36 hours after eating the foodstuffs infected with a Clostridium botulinum culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins,* pages 63–84 (chapter 4) of Natural Toxins II, edited by B. R. Singh et al., Plenum Press, New York (1996) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

[1] Available from Allergan, Inc., of Irvine, Calif. under tradename BODX® in unit vials Seven immunologically distinct botulinum neurotoxins have been characterized, these being respectively botulinum neurotoxin serotypes A, B, $C_1$, D, E, F and G each of which is distinguished by neutralization with typespecific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, and botulinum toxins B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Serotype A and E cleave SNAP-25. Serotype $C_1$ was originally thought to cleave syntaxin, but was found to cleave syntaxin and SNAP-25. Each toxin specifically cleaves a different bond (except tetanus and type B which cleave the same bond).

Botulinum toxins have been used in clinical settings for the treatment of neuromuscular disorders characterized by hyperactive skeletal muscles. Botulinum toxin type A was approved by the U.S. Food and Drug Administration in 1989 for the treatment of blepharospasm, strabismus and hemifacial spasm. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. Biochem,J 1;339 (pt 1):159–65:1999, and Mov Disord, 10(3): 376:1995 (pancreatic islet B cells contain at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., Tetanus Toxin and Botulinum A and C Neurotoxins Inhibit Noradrenaline Release From Cultured Mouse Brain, J Neurochem 51(2);522–527:1988) CGRP, substance P and glutamate (Sanchez-Prieto, J., et al., Botulinum Toxin A Blocks Glutamate Exocytosis From Guinea Pig Cerebral Cortical Synaptosomes, Eur J. Biochem 165;675–681:1987. Thus, when adequate concentrations are used, stimulus-evoked release of most neurotransmitters is blocked by botulinum toxin. See e.g. Pearce, L. B., Pharmacologic Characterization of Botulinum Toxin For Basic Science and Medicine, Toxicon 35(9);1373–1412 at 1393 (1997); Bigalke H., et al., Botulinum A Neurotoxin Inhibits Non-Cholinergic Synaptic Transmission in Mouse Spinal Cord Neurons in Culture, Brain Research 360;318–324:1985; Habermann E., Inhibition by Tetanus and Botulinum A Toxin of the Release of [$^3$H]Noradrenaline and [$^3$H]GABA From Rat Brain Homogenate, Experientia 44;224–226:1988, Bigalke H., et al., Tetanus Toxin and Botulinum A Toxin Inhibit Release and Uptake of Various Transmitters, as Studied with Particulate Preparations From Rat Brain and Spinal Cord, Naunyn-Schmiedeberg's Arch Pharmacol 316;244–251:1981, and; Jankovic J. et al., *Therapy With Botulinum Toxin*, Marcel Dekker, Inc., (1994), page 5.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of Clostridium botulinum with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, Properties and Use of Botulinum Toxin and Other Microbial Neurotoxins in Medicine, Microbiol Rev. 56;80–99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2 \times 10^8$ $LD_{50}$ U/mg or greater; purified botulinum toxin type B with an approximately 156 kD molecular weight with a specific potency of $1-2 \times 10^8$ $LD_{50}$ U/mg or greater, and; purified botulinum toxin type F with an approximately 155 kD molecular weight with a specific potency of $1-2 \times 10^7$ $LD_{50}$ U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St. Louis, Mo.

Pure botulinum toxin is so labile that it is generally not used to prepare a pharmaceutical composition. Furthermore, the botulinum toxin complexes, such as the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) are dependent, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Additionally, the toxin may be used months or years after the toxin containing pharmaceutical composition is formulated. Significantly, it is known that the toxin can be stabilized during the manufacture and compounding processes as well as during storage by use of a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried from. The botulinum toxin type A is made from a culture of the Hall strain of Clostridium botulinum grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below –5° C. BOTOX® can be reconstituted with sterile, non-preserved saline prior to intramuscular injection. Each vial of BOTOX® contains about 100 units (U) of Clostridium botulinum toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® retains its potency for at least two weeks. Neurology, 48:249–53:1997.

It has been reported that botulinum toxin type A has been used in clinical settings as follows:

(1) about 75–125 units of BOTOX® per intramuscular injection (multiple muscles) to treat cervical dystonia;
(2) 5–10 units of BOTOX® per intramuscular injection to treat glabellar lines (brow furrows) (5 units injected intramuscularly into the procerus muscle and 10 units injected intramuscularly into each corrugator supercilii muscle);
(3) about 30–80 units of BOTOX® to treat constipation by intrasphincter injection of the puborectalis muscle;
(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).
(6) to treat upper limb spasticity following stroke by intramuscular injections of BOTOX® into five different upper limb flexor muscles, as follows:
 (a) flexor digitorum profundus: 7.5 U to 30 U
 (b) flexor digitorum sublimus: 7.5 U to 30 U
 (c) flexor carpi ulnaris: 10 U to 40 U
 (d) flexor carpi radialis: 15 U to 60 U
 (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.
(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S111–S1150:1999), and in some circumstances for as long as 27 months, (*The Laryngoscope* 109: 1344–1346:1999). However, the usual duration of an intramuscular injection of Botox® is typically about 3 to 4 months.

The success of botulinum toxin type A to treat a variety of clinical conditions has led to interest in other botulinum toxin serotypes. A study of two commercially available botulinum toxin type A preparations (BOTOX® and Dysport®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX®). Peak muscle weakness and duration were dose related for all serotypes. DAS $ED_{50}$ values (units/kg) were as follows: BOTOX®: 6.7, Dysport®: 24.7, botulinum toxin type B: 27.0 to 244.0, botulinum toxin type F: 4.3. BOTOX® had a longer duration of action than botulinum toxin type B or botulinum toxin type F. Therapeutic index values were as follows: BOTOX®: 10.5, Dysport®: 6.3, botulinum toxin type B: 3.2. Water consumption was greater in mice injected with botulinum toxin type B than with BOTOX®, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX® treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values, the two commercial preparations of botulinum toxin type A (BOTOX® and Dysport®) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage can comprise safety. Furthermore, in rabbits, type B was more antigenic than was BOTOX®, possibly because of the higher protein load injected to achieve an effective dose of botulinum toxin type B. *Eur J Neurol Nov.* 6, 1999 (Suppl 4):S3–S10.

In addition to having pharmacologic actions at a peripheral location, a botulinum toxin can also exhibit a denervation effect in the central nervous system. Wiegand et al, *Naunyn-Schmiedeberg's Arch. Pharmacol.* 1976; 292, 161–165, and Habermann, *Naunyn-Schmiedeberg's Arch. Pharmacol.* 1974; 281, 47–56 reported that botulinum toxin is able to ascend to the spinal area by retrograde transport. As such, a botulinum toxin injected at a peripheral location, for example intramuscularly, can potentially be retrograde transported to the spinal cord.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

Therefore, a need exists for a biocompatible, nonimmunogenic, nonbiodegradable implant which permits long term continuous release of a therapeutically effective neurotoxin in a human patient.

SUMMARY

The present invention meets this need and provides a biocompatible, nonimmunogenic, nonbiodegradable implant which permits long term, continuous release of a neurotoxin in a human patient.

Our invention provides a neurotoxin implant which overcomes the known problems, difficulties and deficiencies associated with repetitive bolus or subcutaneous injection of a neurotoxin, such as a botulinum toxin, to treat an affliction such as a movement disorder, including a muscle spasm.

A controlled release system within the scope of our invention comprises a polymeric matrix, and a quantity of neurotoxin located within the polymeric matrix, wherein fractional amounts of the neurotoxin can be released from the polymeric matrix over a prolonged period of time.

The neurotoxin can be released from the polymeric matrix in a substantially continuous or monophasic manner and the prolonged period of time during which neurotoxin is released from the polymeric matrix can be from 10 days to about 6 years.

The polymeric matrix can be made of a substance which is substantially non-biodegradable and the neurotoxin can be a polypeptide. Additionally, the neurotoxin can be a presynaptic neurotoxin, such as a Clostridial neurotoxin. Further, the neurotoxin can be a botulinum toxin, such as a botulinum toxin selected from the group consisting of botulinum toxin types A, B, $C_1$, D, E, F and G. Preferably, the neurotoxin is a botulinum toxin type A.

The polymer which comprises the polymeric matrix is selected from the group consisting of methacrylate, vinyl pyrrolidone, vinyl alcohol, acrylic acid, siloxane, vinyl acetate, lactic acid, glycolic acid, collagen, and bioceramic polymers and copolymers thereof.

The quantity of the neurotoxin held by the implant is between about 1 unit and about 100,000 units of a botulinum toxin and preferably, from about 1 to about 50,000 units of a botulinum toxin. Thus, the quantity of the neurotoxin can be between about 10 units and about 2,000 units of a botulinum toxin type A and the quantity of the neurotoxin can be between about 100 units and about 30,000 units of a botulinum toxin type B.

The neurotoxin can be a botulinum toxin which is released from the implant in an amount effective to cause flaccid muscular paralysis of a muscle or muscle group at or in the vicinity of the implanted system.

A detailed embodiment of the present invention can be a controlled release system comprising a polymeric matrix, and between about 10 units and about 20,000 units of a botulinum toxin within the polymeric matrix, wherein fractional amounts of the botulinum toxin can be released from the polymeric matrix over a prolonged period of time extending from about 2 months to about 5 years.

A method for making a controlled release system within the scope of our invention can have the steps of (a) dissolving a polymer in a solvent to form a polymer solution; (b) mixing or dispersing a neurotoxin in the polymer solution to form a polymer-neurotoxin mixture, and; (c) allowing the polymer-neurotoxin mixture to set, thereby making a controlled release system. There can also be the step after the mixing step of evaporating solvent.

Additionally, a method for using a continuous release system within the scope of our invention can comprise injection or implantation of a controlled release system which includes a polymeric matrix, thereby treating a movement disorder or a disorder influenced by cholinergic innervation.

Finally, a method for forming a metal cation-complexed neurotoxin comprising the steps of (a) forming a solution containing a neurotoxin; (b) dispersing a multivalent metal cation component with the neurotoxin solution under pH conditions suitable for complexing the multivalent metal cation with the neurotoxin, thereby forming a metal cation-complexed neurotoxin suspension wherein the molar ratio of metal cation component to neurotoxin is between about 4:1 to about 100:1; and; (c) drying said suspension to form the metal cation-complexed neurotoxin.

The amount of a neurotoxin administered by a continuous release system within the scope of the present invention during a given period can be between about $10^{-3}$ U/kg and about 35 U/kg for a botulinum toxin type A and up to about 200 U/kg for other botulinum toxins, such as a botulinum toxin type B. 35 U/kg or 200 U/kg is an upper limit because it approaches a lethal dose of certain neurotoxins, such as botulinum toxin type A and botulinum toxin type B, respectively. Preferably, the amount of the neurotoxin administered by a continuous release system during a given period is between about $10^{-2}$ U/kg and about 25 U/kg. More preferably, the neurotoxin is administered in an amount of between about $10^{-1}$ U/kg and about 15 U/kg. Most preferably, the neurotoxin is administered in an amount of between about 1 U/kg and about 10 U/kg. In many instances, an administration of from about 1 units to about 500 units of a neurotoxin, such as a botulinum toxin type A, provides effective and long lasting therapeutic relief. More preferably, from about 5 units to about 300 units of a neurotoxin, such as a botulinum toxin type A, can be used and most preferably, from about 10 units to about 200 units of a neurotoxin, such as a botulinum toxin type A, can be locally administered into a target tissue with efficacious results. In a particularly preferred embodiment of the present invention from about 1 units to about 100 units of a botulinum toxin, such as botulinum toxin type A, can be locally administered into a target tissue with therapeutically effective results.

The neurotoxin can be made by a Clostridial bacterium, such as by a *Clostridium botulinum, Clostridium butyricum, Clostridium beratti* or *Clostridium tetani* bacterium. Additionally, the neurotoxin can be a modified neurotoxin, that is a neurotoxin that has at least one of its amino acids deleted, modified or replaced, as compared to the native or wild type neurotoxin. Furthermore, the neurotoxin can be a recombinant produced neurotoxin or a derivative or fragment thereof.

The neurotoxin can be a botulinum toxin, such as one of the botulinum toxin serotypes A, B, $C_1$, D, E, F or G. Preferably, the neurotoxin is botulinum toxin type A.

Significantly, the botulinum toxin can be is administered to by subdermal implantation to the patient by placement of a botulinum toxin implant. The botulinum toxin can administered to a muscle of a patient in an amount of between about 1 unit and about 10,000 units. When the botulinum toxin is botulinum toxin type A and the botulinum toxin can be administered to a muscle of the patient in an amount of between about 1 unit and about 100 units.

Notably, it has been reported that glandular tissue treated by a botulinum toxin can show a reduced secretory activity for as long as 27 months post injection of the toxin. *Laryngoscope* 1999; 109:1344–1346, *Laryngoscope* 1998;108:381–384.

Our invention relates to an implant for the controlled release of a neurotoxin and to methods for making and using such implants. The implant can comprise a polymer matrix containing a neurotoxin. The implant is designed to administer effective levels of neurotoxin over a prolonged period of time when administered, for example, intramuscularly, epidurally or subcutaneously for the treatment of various diseases conditions.

This invention further relates to a composition, and methods of making and using the composition, for the controlled of biologically active, stabilized neurotoxin. The controlled release composition of this invention can comprise a polymeric matrix of a biocompatible polymer and biologically active, stabilized neurotoxin dispersed within the biocompatible polymer.

Definitions

The following definitions apply herein.

"Biocompatible" means that there is an insignificant inflammatory response at the site of implantation from use of the implant.

"Biologically active compound" means a compound which can effect a beneficial change in the subject to which it is administered. For example, "biologically active compounds" include neurotoxins.

"Effective amount" as applied to the biologically active compound means that amount of the compound which is generally sufficient to effect a desired change in the subject. For example, where the desired effect is a flaccid muscle paralysis, an effective amount of the compound is that amount which causes at least a substantial paralysis of the desired muscles without causing a substantial paralysis of adjacent muscle of which paralysis is not desired, and without resulting in a significant systemic toxicity reaction.

"Effective amount" as applied to a non-active ingredient constituent of an implant (such as a polymer used for forming a matrix or a coating composition) refers to that amount of the non-active ingredient constituent which is sufficient to positively influence the release of a biologically active agent at a desired rate for a desired period of time. For example, where the desired effect is muscle paralysis by using a single implant, the "effective amount" is the amount that can facilitate extending the release over a period of between about 60 days and 6 years. This "effective amount" can be determined based on the teaching in this specification and the general knowledge in the art.

"Effective amount" as applied to the amount of surface area of an implant is that amount of implant surface area which is sufficient to effect a flux of biologically active compound so as to achieve a desired effect, such as a muscle paralysis. The area necessary may be determined and adjusted directly by measuring the release obtained for the particular active compound. The surface area of the implant or of a coating of an implant is that amount of membrane necessary to completely encapsulate the biologically active compound. The surface area depends on the geometry of the implant. Preferably, the surface area is minimized where possible, to reduce the size of the implant.

"Implant" means a controlled release drug delivery system. The implant is comprised of a biocompatible polymer or ceramic material which contains or which can act as a carrier for a molecule with a biological activity. The implant can be, injected, inserted or implanted into a human body.

"Local administration" means direct administration of a biologically active compound, such as a therapeutic drug to a tissue by a non-systemic route. Local administration therefore includes, subcutaneous, intramuscular, intraspinal (i.e. intrathecal and epidural), intracranial, and intraglandular administration. Local administration excludes a systemic route of administration such as oral or intravenous administration.

"Neurotoxin" means an agent which can interrupt nerve impulse transmission across a neuromuscular or neuroglandular junction, block or reduce neuronal exocytosis of a neurotransmitter or alter the action potential at a sodium channel voltage gate of a neuron. Examples of neurotoxins include botulinum toxins, tetanus toxins, saxitoxins, and tetrodotoxin.

"Treatment" means any treatment of a disease in a mammal, and includes: (i) preventing the disease from occurring or; (ii) inhibiting the disease, i.e., arresting its development; (iii) relieving the disease, i.e., reducing the incidence of symptoms of or causing regression of the disease.

A method for making an implant within the scope of the present invention for controlled release of a neurotoxin, can include dissolving a biocompatible polymer in a polymer solvent to form a polymer solution, dispersing particles of biologically active, stabilized neurotoxin in the polymer solution, and then solidifying the polymer to form a polymeric matrix containing a dispersion of the neurotoxin particles.

A method of using an implant within the scope of the present invention forming for controlled release of a neurotoxin can comprise providing a therapeutically effective level of biologically active, neurotoxin in a patient for a prolonged period of time by implanting in the patient the implant.

DESCRIPTION

The present invention is based upon the discovery that a continuous release, implant comprising a biocompatible, non-biodegradable or biodegradable polymer can exhibit prolonged in vivo release of therapeutic amounts of a neurotoxin.

An implant within the scope of our invention can be surgically inserted by incision at the site of desired effect (i.e. for reduction of a muscle spasm) or the implant can be administered subcutaneously or intramuscularly using a hollow needle implanting gun, for example of the type disclosed in U.S. Pat. No. 4,474,572. The diameter of the needle may be adjusted to correspond to the size of the implant used. Further, an implant within the scope of the present invention can be implanted intracranially so as to provide long term delivery of a therapeutic amount of a neurotoxin to a target brain tissue. Removal of a non-biodegradable implant within the scope of the present invention is not necessary once the implant has been spent, since the implant is comprised of a biocompatible, nonimmunogenic material.

To stabilize a neurotoxin, both in a format which renders the neurotoxin useful for mixing with a suitable polymer which can form the implant matrix (i.e. a powdered neurotoxin which has been freeze dried or lyophilized) as well as while the neurotoxin is present or incorporated into the matrix of the selected polymer, various pharmaceutical excipients can be used. Suitable excipients can include starch, cellulose, talc, glucose, lactose, sucrose, gelatin, malt, rice, flour, chalk, silica gel, magnesium stearate, sodium stearate, glycerol monostearate, sodium chloride and dried skim milk.

The thickness of the implant can be used to control the absorption of water by, and thus the rate of release of a neurotoxin from, a composition of the invention, thicker implants releasing the polypeptide more slowly than thinner ones.

The implant can rapidly release a suboptimal amount of neurotoxin during a first phase, the burst period. The burst period typically lasts less than 24 hours and frequently extends over only about an hour or so after implantation. Thereafter the amount of neurotoxin released by the implant rapidly declines and stabilizes at a much reduced and, significantly, relatively constant (i.e. zero order kinetics) level of released neurotoxin. This second, prolonged phase of neurotoxin release can extend over a period of from about one year to about five or six years. An initial portion of the second phase can be termed the make up period.

The additive amount of neurotoxin released during the burst phase and the make up period is preferably equal to an optimal amount of neurotoxin so as to treat a particular disorder or affliction. The temporal extent of the make up period is somewhat less than the period of time upon the expiry of which an optimal administration of the neurotoxin shows significantly reduced efficacy. For example, to treat upper limb spasticity the optimal amount of intramuscular botulinum toxin type A can be about 90 units injected into the biceps brachii muscle. Typically, the flaccid paralysis so induced within 1–7 days of a bolus injection substantially wears off after about 3 months. A subdermal neurotoxin implant within the scope of our invention can be configured to release about 60 units of botulinum toxin type essentially immediately upon implantation (i.e. during the burst period). This suboptimal amount of neurotoxin provides rapid and substantial relief. During phase 2 the implant continuously releases about 0.4 unit/day of a neurotoxin, such as a botulinum toxin type A, so that after about 75 days the optimal amount of 90 units has been released by the implant into the target tissue.

The pre-synaptic neuronal receptor for which botulinum toxin exhibits a high and specific affinity has not been identified. Nor has a generally accepted mechanism to account for the long intraneuronal half life of botulinum toxin been elucidated. Nevertheless it is known that a dynamic process, which may be either unblocking, reappearance, resynthesis and/or reactivation of the botulinum toxin receptor or the appearance of new neural sprouts, or both, transpires and accounts for the gradual wearing off of the paralytic effect which results from an administration of a botulinum toxin. Thus, while in the example above it can take 75 days for an optimal amount (total of 90 units) of botulinum toxin to be released by the implant, due to the dynamic nature of the attenuation of the effect of the botulinum toxin, subsequent release of toxin (i.e. beyond 75 days) by the implant does not result in unwanted or excess areas of paralysis. Thus, it can be expected, in this example, that toxin released by the implant on day 76 binds to the new receptors and/or neutral sprouts formed in response to the denervation caused by the toxin released by the implant on or about day one. The rolling nature of the denervation process means that, rather than resulting in excess toxin which can diffuse systemically or cause unwanted paralysis, the continuous release of toxin after the end of the make up period simply again denervates within the same desired muscle location. Thus, assuming a spherical pattern of clenervation and holding other factors constant, the burst release denervates a sphere of tissue with a diameter about 2/3 the optimal size of the tissue mass for which denervation is desired. Later release of neurotoxin during the make up period and subsequent provides the optimal or desired extent of tissue denervation and amounts of neurotoxin to renew denervation at recently renervated sites within the target tissue.

It is known that blepharospasm can be treated by intramuscular injection of about 5 units (repeated at 2–4 month intervals) of botulinum toxin type A into the lateral pre-tarsal orbicularis oculi muscle. Significantly, a single implant within the scope of our invention can be used for the treatment of blepharospasm over, for example, a one-year period. With this affliction and a one year period chosen for treatment by implant release of neurotoxin, and a 15% burst characteristic polymer used, the total neurotoxin loading into the implant can be 20 units. During the burst period about 3 units of the toxin is released (within 24 hours after implantation) followed by a continuous release of about 0.0467 units per day (i.e. about 2.3 picograms of BOTOX® released per day). Thus, by day 42 about 5 units total of the neurotoxin has been released. The release rate in this example (15% burst, remaining 85% over 364 days) is 0.234%/day. In this example, on day 1 the patient receives a 20 unit implant and one year later the patient has the spent implant removed and another 20 unit implant inserted. Thus 25 units are administered over 365 days, with effect of second implant on day 365 included.

Since one mole (M) of the botulinum toxin type A complex contains about $9 \times 10^5$ grams, therefore one picogram (pg) of the botulinum toxin type A complex is about $1.1 \times 10^{-18}$ M. Hence, a desired release of 0.234%/day of total incorporated neurotoxin equals a release of about $2.53 \times 10^{-18}$ M/day. With one year treatment period, 20% burst, followed by 80% over 364 days results in a controlled release of about 0.22%/day or 0.044 units/day or 2.2 picograms/day or about $2.42 \times 10^{-18}$ M/day. A 20% burst from a 20 unit implant provides 4 units of the neurotoxin in about the first 24 hours after implantation. Generally, surface area of the implant is equal to x units of toxin released/day for each y $cm^2$ of implant surface area.

Different conditions are treated with botulinum toxin injection ranging from about 5 units to about 100 units per injection. A typical implant to treat, over a one year period, a condition for which 25 units of type A is the optimal bolus dose can be loaded with 100 units of a botulinum toxin type A complex. The burst can be 20%, followed by 80% over 364 days, which is equal to 0.22%/day or 0.22 units/day or 11 picograms/day or about $1.21 \times 10^{-17}$ M/day For a five year treatment period, that is 20 bolus injections of 25 units, the first injection is at time zero, and the $20^{th}$ injection is at month 57, for a 500 unit total series of injections. Contrarily, with our invention, a 5 year implant to treat a condition responsive to 25 units of a botulinum toxin, such as a botulinum toxin type A, can be made with a 500 toxin unit loaded implant with the characteristics of a 20 unit burst (4% burst), followed by about 480 units released over about 1736 days, which is equal to 0.267 unit/day or $5.56 \times 10^{-4}$%/day or 13.35 picograms/day released by the implant.

A matrix implant can be made by dissolving a selected polymer in an appropriate solvent. Into this casting solution the desired amount of lyophilized or freeze dried, powered neurotoxin (i.e. the total desired amount of the neurotoxin, such as non-reconstituted BOTOX®, to be released over the therapeutic period) is mixed. This method can be used to make coated implant pellets, with the modification that the coating used in an embodiment of the present invention is a bioerodible polymer which is impermeable to the neurotoxin. Thus, the neurotoxin does not diffuse out of the matrix into the surrounding tissue until the coating has degraded.

The pH of the casting or other solution in which the botulinum toxin is to be mixed is maintained at pH 4.2–6.8, because at pH above 7 the stabilizing nontoxin proteins dissociate from the botulinum toxin resulting in gradual loss of toxicity. Preferably, the pH is between about 5–6. Furthermore the temperature of the mixture/solution should not exceed about 35 degrees Celsius, because the toxin is readily detoxified when in a solution/mixture heated above about 40 degrees Celsius.

Suitable implants within the scope of the present invention for the controlled in vivo release of a neurotoxin, such as a botulinum toxin, can be prepared so that the implant releases the neurotoxin in either a continuous or in a pulsatile fashion. "Continuous release" means release of toxin in a substantially monophasic manner, after the initial burst phase. A continuous release can have a point of inflection, but not a plateau phase. Continuous release does not require a release from the implant of a similar amount of a neurotoxin per unit if time. A pulsatile release implant can release a neurotoxin is a biphasic or multiphase manner. Thus, a pulsatile release implant can have a relatively short initial induction (burst) period, followed by periods during which little or no neurotoxin is released.

A controlled release of biologically active neurotoxin is a release which results in therapeutically effective, with negligible serum levels, of biologically active, neurotoxin over a period longer than that obtained following direct administration of aqueous neurotoxin. It is preferred that a controlled release be a release of neurotoxin for a period of about six months or more, and more preferably for a period of about one year or more.

Suitable implants within the scope of the present invention for the controlled in vivo release of a neurotoxin, such as a botulinum toxin, can exhibit a continuous release or a pulsatile release of the neurotoxin. Additionally, the implant can comprise a non-biodegradable or a biodegradable polymeric material. Significantly, our invention encompasses: (1) continuous release, nonbiodegradable neurotoxin implants; (2) continuous release, biodegradable neurotoxin implants; (3) pulsatile release, nonbiodegradable neurotoxin implants, and; (4) pulsatile release, biodegradable implants, and each of these four types of encompasses implant can be formulated into a variety of conformations, suitable for subdermal injection or implantation such as pellets, discs, microspheres, films, rods and tubes, each of which can have, for example, one or more coatings over a reservoir or matrix structure.

An implant within the scope of our invention can also be formulated as a suspension for injection. Such suspensions may be manufactured by general techniques well known in the pharmaceutical art, for example by milling the polylactide/polypeptide mixture in an ultracentrifuge mill fitted with a suitable mesh screen, for example a 120 mesh, and suspending the milled, screened particles in a solvent for injection, for example propylene glycol, water optionally with a conventional viscosity increasing or suspending agent, oils or other known, suitable liquid vehicles for injection.

Denaturation of the encapsulated neurotoxin in the body at 37 degrees C. for a prolonged period of time can be reduced by stabilizing the neurotoxin by lyophilizing it with albumin, lyophilizing from an acidic solution, lyophilizing from a low moisture content solution (these three criteria can be met with regard to a botulinum toxin type A by use of non-reconstituted Botox®) and using a specific polymer matrix composition.

Preferably, the release of biologically active neurotoxin in vivo does not result in a significant immune system response during the release period of the neurotoxin.

Matrix Stabilized Neurotoxin

We have discovered that a stabilized neurotoxin can comprise biologically active, non-aggregated neurotoxin complexed with at least one type of multivalent metal cation which has a valiancy of +2 or more.

Suitable multivalent metal cations include metal cations contained in biocompatible metal cation components. A metal cation component is biocompatible if the cation component is non-toxic to the recipient, in the quantities used, and also presents no significant deleterious or untoward effects on the recipient's body, such as an immunological reaction at the injection site.

Preferably, the molar ratio of metal cation component to neurotoxin, for the metal cation stabilizing the neurotoxin, is between about 4:1 to about 100:1 and more typically about 4:1 to about 10:1.

A preferred metal cation used to stabilize neurotoxin is $Zn^{++}$. Divalent zinc cations are preferred because botulinum toxin is known to be a divalent zinc endopeptidase. In a more preferred embodiment, the molar ratio of metal cation component, containing $Zn^{++}$ cations, to neurotoxin is about 6:1.

The suitability of a metal cation for stabilizing neurotoxin can be determined by one of ordinary skill in the art by performing a variety of stability indicating techniques such as polyacrylamide gel electrophoresis, isoelectric focusing, reverse phase chromatography, HPLC and potency tests on neurotoxin lyophilized particles containing metal cations to determine the potency of the neurotoxin after lyophilization and for the duration of release from microparticles. In stabilized neurotoxin, the tendency of neurotoxin to aggregate within a microparticle during hydration in vivo and/or to lose biological activity or potency due to hydration or due to the process of forming is a controlled release composition, or due to the chemical characteristics of a controlled release composition, is reduced by complexing at least one type of metal cation with nelrotoxin prior to contacting the neurotoxin with a polymer solution.

By our invention, stabilized neurotoxin is stabilized against significant aggregation in vivo over the controlled release period. Significant aggregation is defined as an amount of aggregation resulting in aggregation of about 15% or more of the polymer encapsulated or polymer matrix incorporated neurotoxin. Preferably, aggregation is maintained below about 5% of the neurotoxin. More preferably, aggregation is maintained below about 2% of the neurotoxin present in the polymer.

The neurotoxin in a neurotoxin controlled release composition can also be mixed with other excipients, such as bulking agents or additional stabilizing agents, such as buffers to stabilize the neurotoxin during lyophilization.

Bulking agents typically comprise inert materials. Suitable bulking agents are known to those skilled in the art.

A polymer, or polymeric matrix, suitable for the controlled release composition of the present invention, must be biocompatible. A polymer is biocompatible if the polymer, and any degradation products of the polymer, are non-toxic to the recipient and also present no significant deleterious or untoward effects on the recipient's body, such as an immunological reaction at the injection site.

The polymer of the neurotoxin controlled release composition can be made of a biodegradable material. Biodegradable, as defined herein, means the composition will degrade or erode in vivo to form smaller chemical species. Degradation can result, for example, by enzymatic, chemical and physical processes.

Suitable biocompatible, biodegradable polymers include, for example, poly(lactides), poly(glycolides), poly(lactide-co-glycolides), poly(lactic acid)s, poly(glycolic acid)s, poly (lactic acid-co-glycolic acid)s, polycaprolactone, polycarbonates, polyesteramides, polyanhydrides, poly (amino acids), polyorthoesters, polycyanoacrylates, poly(p-dioxanone), poly(alkylene oxalates), biodegradable polyurethanes, blends and copolymers thereof.

Further, the terminal functionalities of the polymer can be modified. For example, polyesters can be blocked, unblocked or a blend of blocked and unblocked polymers. A blocked polymer is as classically defined in the art, specifically having blocked carboxyl end groups. Generally, the blocking group is derived from the initiator of the polymerization and is typically an alkyl group. An unblocked polymer generally has free carboxyl end groups.

Acceptable molecular weights for a biodegradable polymer used in this invention can be determined by a person of ordinary skill in the art taking into consideration factors such as the desired polymer degradation rate, physical properties such as mechanical strength, and rate of dissolution of polymer in solvent. Typically, an acceptable range of molecular weights is of about 2,000 Daltons to about 2,000,000 Daltons. In a preferred embodiment, the polymer is a biodegradable polymer or copolymer. In a more preferred embodiment, the polymer is a poly(lactide-co-glycolide) (hereinafter "PLGA") with a lactide:glycolide ratio of about 1:1 and a molecular weight of about 5,000 Daltons to about 70,000 Daltons. In an even more preferred embodiment, the molecular weight of the PLGA used in the present invention has a molecular weight of about 6,000 to about 31,000 Daltons.

The amount of neurotoxin, which is contained in a dose of controlled release microparticles, or in an alternate controlled release system, containing biologically active, stabilized neurotoxin particles is a therapeutically or prophylactically effective amount, which can be determined by a person of ordinary skill in the art taking into consideration factors such as body weight, condition to be treated, type of polymer used, and release rate from the polymer.

In one embodiment, a neurotoxin controlled release composition contains from about $10^{-4}\%$ (w/w) to about 1% (w/w) of biologically active, stabilized neurotoxin. The amount of such neurotoxin particles used will vary depending upon the desired effect of the neurotoxin, the planned release levels, the times at which neurotoxin should be released, and the time span over which the neurotoxin will be released. A preferred range of neurotoxin particle loading is between about $10^{-4}\%$ (w/w) to about 0.1% (w/w) neurotoxin particles. A more preferred range of neurotoxin loading is between about $10^{-3}\%$ (w/w) to about 1% (w/w) neurotoxin. The most preferred loading of the biologically active, stabilized neurotoxin particles is about $10^{-2}\%$ (w/w).

In another embodiment, a neurotoxin controlled release composition also contains a second metal cation component, which is not contained in the stabilized neurotoxin particles, and which is dispersed within the polymer. The second metal cation component preferably contains the same species of metal cation, as is contained in the stabilized neurotoxin. Alternately, the second metal cation component can contain one or more different species of metal cation.

The second metal cation component acts to modulate the release of the neurotoxin from the polymeric matrix of the controlled release composition, such as by acting as a reservoir of metal cations to further lengthen the period is of time over which the neurotoxin is stabilized by a metal cation to enhance the stability of neuroltoxin in the composition.

A metal cation component used in modulating release typically contains at least one type of multivalent metal cation. Examples of second metal cation components suitable to modulate neurotoxin release, include, or contain, for instance, $Mg(OH)_2$, $MgCO_3$ (such as $4MgCO_3Mg(OH)_25H_2O$), $ZnCO_3$ (such as $3Zn(OH)_22ZnCO_3$), $CaCO_3$, $Zn_3(C_6H_5O_7)_2$, $Mg(OAc)_2$, $MgSO_4$, $Zn(OAc)_2$, $ZnSO_4$, $ZnCl_2$, $MgCl$, and $Mg_3(C_6H_5O_7)_2$. A suitable ratio of second metal cation component-to-polymer is between about 1:99 to about 1:2 by weight. The optimum ratio depends upon the polymer and the second metal cation component utilized.

The neurotoxin controlled release composition of this invention can be formed into many shapes such as a film, a pellet, a cylinder, a disc or a microparticle. A microparticle, as defined herein, comprises a polymeric component having a diameter of less than about one millimeter and having stabilized neurotoxin particles dispersed therein. A microparticle can have a spherical, non-spherical or irregular shape. It is preferred that a microparticle be a microsphere. Typically, the microparticle will be of a size suitable for injection. A preferred size range for microparticles is from about 1 to about 180 microns in diameter.

In the method of this invention for forming a composition for the controlled release of biologically active, non-aggregated neurotoxin, a suitable amount of particles of biologically active, stabilized neurotoxin are dispersed in a polymer solution.

A suitable polymer solution contains between about 1% (w/w) and about 30% (w/w) of a suitable biocompatible polymer, wherein the biocompatible polymer is typically dissolved in a suitable polymer solvent. Preferably, a polymer solution contains about 2% (w/v) to about 20% (w/v) polymer. A polymer solution containing 5% to about 10% (w/w) polymer is most preferred.

A suitable polymer solvent, as defined herein, is solvent in which the polymer is soluble but in which the stabilized neurotoxin particles are substantially insoluble and non-reactive. Examples of suitable polymer solvents include polar organic liquids, such as methylene chloride, chloroform, ethyl acetate and acetone.

To prepare biologically active, stabilized neurotoxin, neurotoxin is mixed in a suitable aqueous solvent with at least one suitable metal cation component under pH conditions suitable for forming a complex of metal cation and neurotoxin. Typically, the complexed neurotoxin will be in the form of a cloudy precipitate, which is suspended in the solvent. However, the complexed neurotoxin can also be in solution. In an even more preferred embodiment, neurotoxin is complexed with $Zn^{++}$.

Suitable pH conditions to form a complex of neurotoxin typically include pH values between about 5.0 and about 6.9. Suitable pH conditions are typically achieved through use of an aqueous buffer, such as sodium bicarbonate, as the solvent.

Suitable solvents are those in which the neurotoxin and the metal cation component are each at least slightly soluble, such as in an aqueous sodium bicarbonate buffer. For aqueous solvents, it is preferred that water used be either deionized water or water-for-injection (WFI).

The neurotoxin can be in a solid or a dissolved state, prior to being contacted with the metal cation component. Additionally, the metal cation component can be in a solid or a dissolved state, prior to being contacted with the neurotoxin. In a preferred embodiment, a buffered aqueous solution of neurotoxin is mixed with an aqueous solution of the metal cation component.

Typically, the complexed neurotoxin will be in the form of a cloudy precipitate, which is suspended in the solvent. However, the complexed neurotoxin can also be in solution. In a preferred embodiment, the neurotoxin is complexed with $Zn^{++}$.

The $Zn^{++}$ complexed neurotoxin can then be dried, such as by lyophilization, to form particulates of stabilized neurotoxin. The $Zn^{++}$ complexed neurotoxin, which is suspended or in solution, can be bulk lyophilized or can be divided into smaller volumes which are then lyophilized. In a preferred embodiment, the $Zn^{++}$ complexed neurotoxin suspension is micronized, such as by use of an ultrasonic nozzle, and then lyophilized to form stabilized neurotoxin particles. Acceptable means to lyophilize the $Zn^{++}$ complexed neurotoxin mixture include those known in the art.

Preferably, particles of stabilized neurotoxin are between about 1 to about 6 micrometers in diameter. The neurotoxin particles can be fragmented separately, Alternately, the neurotoxin particles can be fragmented after being added to a polymer solution, such as by means of an ultrasonic probe or ultrasonic nozzle.

In another embodiment, a second metal cation component, which is not contained in the stabilized neurotoxin particles, is also dispersed within the polymer solution.

It is understood that a second metal cation component and stabilized neurotoxin can be dispersed into a polymer solution sequentially, in reverse order, intermittently, separately or through concurrent additions. Alternately, a polymer, a second metal cation component and stabilized neurotoxin and can be mixed into a polymer solvent sequentially, in reverse order, intermittently, separately or through concurrent additions.

In this method, the polymer solvent is then solidified to form a polymeric matrix containing a dispersion of stabilized neurotoxin particles.

A suitable method for forming an neurotoxin controlled release composition from a polymer solution is the solvent evaporation method is described in U.S. Pat. Nos. 3,737,337; 3,523,906; 3,691,090, and; 4,389,330. Solvent evaporation can be used as a method to form neurotoxin controlled release microparticles.

In the solvent evaporation method, a polymer solution containing a stabilized neurotoxin particle dispersion, is mixed in or agitated with a continuous phase, in which the polymer solvent is partially miscible, to form an emulsion. The continuous phase is usually an aqueous solvent. Emulsifiers are often included in the continuous phase to stabilize the emulsion. The polymer solvent is then evaporated over a period of several hours or more, thereby solidifying the polymer to form a polymeric matrix having a dispersion of stabilized neurotoxin particles contained therein.

A preferred method for forming neurotoxin controlled release microparticles from a polymer solution is described in U.S. Pat. No. 5,019,400. This method of microsphere formation, as compared to other methods, such as phase separation, additionally reduces the amount of neurotoxin required to produce a controlled release composition with a specific neurotoxin content.

In this method, the polymer solution, containing the stabilized neurotoxin particle dispersion, is processed to create droplets, wherein at least a significant portion of the droplets contain polymer solution and the stabilized neurotoxin particles. These droplets are then frozen by means suitable to form microparticles. Examples of means for processing the polymer solution dispersion to form droplets include directing the dispersion through an ultrasonic nozzle, pressure nozzle, Rayleigh jet, or by other known means for creating droplets from a solution.

Means suitable for freezing droplets to form microparticles include directing the droplets into or near a liquefied gas, such as liquid argon and liquid nitrogen to form frozen microdroplets which are then separated from the liquid gas. The frozen microdroplets are then exposed to a liquid non-solvent, such as ethanol, or ethanol mixed with hexane or pentane.

The solvent in the frozen microdroplets is extracted as a solid and/or liquid into the non-solvent to form stabilized neurotoxin containing microparticles. Mixing ethanol with other non-solvents, such as hexane or pentane, can increase the rate of solvent extraction, above that achieved by ethanol alone, from certain polymers, such as poly(lactide-co-glycolide) polymers.

A wide range of sizes of neurotoxin controlled release microparticles can be made by varying the droplet size, for example, by changing the ultrasonic nozzle diameter. If very large microparticles are desired, the microparticles can be extruded through a syringe directly into the cold liquid. Increasing the viscosity of the polymer solution can also increase microparticle size. The size of the microparticles can be produced by this process, for example microparticles ranging from greater than about 1000 to about 1 micrometers in diameter.

Yet another method of forming a neurotoxin controlled release composition, from a polymer solution, includes film casting, such as in a mold, to form a film or a shape. For instance, after putting the polymer solution containing a dispersion of stabilized neurotoxin particles into a mold, the polymer solvent is then removed by means known in the art, or the temperature of the polymer solution is reduced, until a film or shape, with a consistent dry weight, is obtained.

In the case of a biodegradable polymer implant, release of neurotoxin due to degradation of the polymer. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; and the molecular weight of the polymer. These properties can affect hydrophilicity and crystallinity, which control the rate of hydration of the polymer. Hydrophilic excipients such as salts, carbohydrates and surfactants can also be incorporated to increase hydration and which can alter the rate of erosion of the polymer.

By altering the properties of a biodegradable polymer, the contributions of diffusion and/or polymer degradation to neurotoxin release can be controlled. For example, increasing the glycolide content of a poly(lactide-co-glycolide) polymer and decreasing the molecular weight of the polymer can enhance the hydrolysis of the polymer and thus, provides an increased neurotoxin release from polymer erosion. In addition, the rate of polymer hydrolysis is increased in non-neutral pH's. Therefore, an acidic or a basic excipient can be added to the polymer solution, used to form the microsphere, to alter the polymer erosion rate.

The composition of our invention can be administered to a human, or other animal, by any non-system means of administration, such as by implantation (e.g. subcutaneously, intramuscularly, intracranially, intravaginally and intradermally), to provide the desired dosage of neurotoxin based on the known parameters for treatment with neurotoxin of various medical conditions.

The specific dosage by implant appropriate for administration is readily determined by one of ordinary skill in the art according to the factor discussed above. The dosage can also depend upon the size of the tissue mass to be treated or denervated, and the commercial preparation of the toxin. Additionally, the estimates for appropriate dosages in humans can be extrapolated from determinations of the amounts of botulinum required for effective denervation of other tissues. Thus, the amount of botulinum A to be injected is proportional to the mass and level of activity of the tissue to be treated. Generally, between about 0.01 units per kilogram to about 35 units per kg of patient weight of a botulinum toxin, such as botulinum toxin type A, can be released by the present implant per unit time period (i.e. over a period of or once every 2–4 months) to effectively accomplish a desired muscle paralysis. Less than about 0.01 U/kg of a botulinum toxin does not have a significant therapeutic effect upon a muscle, while more than about 35 U/kg of a botulinum toxin approaches a toxic dose of a neurotoxin, such as a botulinum toxin type A. Careful preparation and placement of the implant prevents significant amounts of a botulinum toxin from appearing systemically. A more preferred dose range is from about 0.01 U/kg to about 25 U/kg of a botulinum toxin, such as that formulated as BOTOX®. The actual amount of U/kg of a botulinum toxin to be administered depends upon factors such as the extent (mass) and level of activity of the tissue to be treated and the administration route chosen. Botulinum toxin type A is a preferred botulinum toxin serotype for use in the methods of the present invention.

Preferably, a neurotoxin used to practice a method within the scope of the present invention is a botulinum toxin, such as one of the serotype A, B, C, D, E, F or G botulinum toxins. Preferably, the botulinum toxin used is botulinum toxin type A, because of its high potency in humans, ready availability, and known safe and efficacious use for the treatment of skeletal muscle and smooth muscle disorders when locally administered by intramuscular injection.

The present invention includes within its scope the use of any neurotoxin which has a long duration therapeutic effect when used to treat a movement disorder or an affliction influenced by cholinergic innervation. For example, neurotoxins made by any of the species of the toxin producing Clostridium bacteria, such as *Clostridium botulinum, Clostridium butyricum,* and *Clostridium beratti* can be used or adapted for use in the methods of the present invention. Additionally, all of the botulinum serotypes A, B, C, D, E, F and G can be advantageously used in the practice of the present invention, although type A is the most preferred serotype, as explained above. Practice of the present invention can provide effective relief for from 1 month to about 5 or 6 years.

The present invention includes within its scope: (a) neurotoxin complex as well as pure neurotoxin obtained or processed by bacterial culturing, toxin extraction, concentration, preservation, freeze drying and/or reconstitution and; (b) modified or recombinant neurotoxin, that is neurotoxin that has had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made, and includes neurotoxins with one or more attached targeting moieties for a cell surface receptor present on a cell.

Botulinum toxins for use according to the present invention can be stored in lyophilized or vacuum dried form in containers under vacuum pressure. Prior to lyophilization the botulinum toxin can be combined with pharmaceutically acceptable excipients, stabilizers and/or carriers, such as albumin. The lyophilized or vacuum dried material can be reconstituted with saline or water.

Our invention also includes within its scope the use of an implanted controlled release neurotoxin complex so as to provide therapeutic relief from a chronic disorder such as movement disorder. Thus, the neurotoxin can be imbedded within, absorbed, or carried by a suitable polymer matrix which can be implanted or embedded subdermally so as to provide a year or more of delayed and controlled release of the neurotoxin to the desired target tissue. Implantable polymers which permit controlled release of polypeptide drugs are known, and can be used to prepare a botulinum toxin implant suitable for insertion or subdermal attachment. See e.g. Pain 1999;82(1):49–55; Biomaterials 1994;15(5):383–9; Brain Res 1990;515(1–2):309–11 and U.S. Pat. Nos. 6,022,554; 6,011,011; 6,007,843; 5,667,808, and; 5,980,945.

Methods for determining the appropriate route of administration and dosage are generally determined on a case by case basis by the attending physician. Such determinations are routine to one of ordinary skill in the art (see for example, Harrison's Principles of Internal Medicine (1998), edited by Anthony Fauci et al., $14^{th}$ edition, published by McGraw Hill).

EXAMPLES

The following examples set forth specific compositions and methods encompassed by the present invention and are not intended to limit the scope of our invention.

Example 1

Formation of $Zn^{++}$ Stabilized Neurotoxin

One hundred units of a neurotoxin, such as unreconstituted Botox®, is dissolved in sodium bicarbonate buffer (pH 6.0) to form a neurotoxin solution. A $Zn^{++}$ solution is prepared from deionized water and zinc acetate dihydrate and then added with gentle mixing to the neurotoxin solution to form a $Zn^{++}$ neurotoxin complex. The pH of the $Zn^{++}$ neurotoxin complex is then adjusted to between 6.5 and 6.9 by adding 1% acetic acid. A cloudy suspended precipitate, comprising insoluble $Zn^{++}$ stabilized neurotoxin is thereby formed. There is thereby made a neurotoxin (such as a botulinum toxin type A) complex stabilized against significant aggregation upon subsequent incorporation into a polymeric implant matrix.

Example 2

Neurotoxin Controlled Release Pellet

A neurotoxin suitable for incorporation into a polymer or polymerizable solution can be a botulinum toxin type A (such as Botox®), which is commercially available as a freeze dried powder. Additionally, various polymers and copolymers can be mixed and stored in a dry state with no effect on final implant performance. For example, an acrylate copolymer using an UV cured initiator. The neurotoxin can be complexed with $Zn^{++}$ as set forth in Example 1 above. The $Zn^{+'}$ stabilized neurotoxin complex is then mixed with uncured acrylate copolymer, UV initiator and an acid (pH between 5.5 and 6.8). The mixture is placed into a glass or clear plastic pellet mold is which allows penetration of UV light. The mold is placed into a temperature controlled water bath held at 20 C. The pellet is cured with UV light for approximately 50 seconds, packaged and sterilized. The duration and intensity of the UV curing are such that insignificant amount of neurotoxin are disrupted or denatured.

The size of the pellet and the concentration of the amount of neurotoxin inside of the pellet are defined by the desired application. When the pellet is implanted, the pellet is hydrated inside of the body, which slightly delays the initial burst of the neurotoxin from inside of the implant. Coating the outside of the pellet with a portion of the desired initial burst concentration of neurotoxin can offset this delay. In this example the pellet effectiveness would be for approximately about 4 to about 6 months.

Example 3

Neurotoxin Controlled Release Formulations

To increase the amount of time the pellet can effectively deliver neurotoxin, multiple layers of materials can be used. Thus, the inner material can be made from a polyvinylpyrrolidone/methylmethacrylate copolymer. This material allows for sustaining a high concentration of neurotoxin complex. A suitable amount of neurotoxin is complexed with $Zn^{++}$ as set forth in Example 1 above and this complex is then mixed with uncured copolymer, low temperature initiator and an acid (pH between 5.5 and 6.8). The mixture is placed into a glass or plastic pellet mold. The mold is placed into a temperature controlled water bath at about 35 degrees C. for between about 6 hours and about 8 hours. This forms the reservoir of neurotoxin required for a prolonged, controlled release.

In order to prolong the release of the neurotoxin a second material is then cured around the initial pellet. This material is chosen for high molecular density and biocompatibility. Polymethylmethacrylate (PMMA) is an example of a material with this characteristic. The pellet (above) is placed into a mold (insertion molding) with uncured PMMA/low temperature initiator. A secondary coating of the uncured PMMA maybe necessary to assure uniform coating of the pellet. Preferably, the PMMA thickness is 0.5 mm. After forming, the outside of the pellet is coated with the desired initial burst concentration of neurotoxin. The PMMA layer will be sufficiently thick to allow for a delay (up to 3 months) of the neurotoxin in the reservoir. When the neurotoxin reaches the surface of the implant a second large burst of neurotoxin is obtained. This secondary burst will then be followed by a slowly decreasing release rate of the neurotoxin for approximately 3 months. In this example the pellet effectiveness is for about 7 to about 9 months.

Example 4

Multi Layer Neurotoxin Controlled Release Implant

By utilizing multiple layers—high density polymer/low density polymer w/neurotoxin—the temporal extent of the controlled release of a neurotoxin can be increased, but the size of the implant can also increase. As the size of the implant is increased the neurotoxin disperses over a greater area inside of the body, which can decrease the effectiveness of the implant. In order to avoid this, the implant is encased by a non-permeable material such as titanium. A small opening is kept to allow for pinpoint release of the neurotoxin through the encased pellet. This effectively can generally allow the implant to have significantly different release characteristics. Essentially this can also allow for thicker section of polymer the neurotoxin will pass, effectively increasing the duration of the neurotoxin release.

The inner material can be made from a material such as polyvinylpyrrolidone/methylmethacrylate copolymer. This material allows for sustaining a high concentration of neurotoxin complex. The neurotoxin is complexed with $Zn^{++}$. The complex is then mixed with uncured copolymer, low temperature initiator and an acid (pH between 5.5 and 6.8). The mixture is placed into a glass or plastic pellet mold. The mold is placed into a temperature controlled water bath at 35 degrees C. for between about 6 and about 8 hours. This forms the reservoir of neurotoxin required for a prolonged controlled release.

In order to prolong the release of the neurotoxin a second material is then cured around the initial pellet. The pellet (above) is placed into a mold (insertion molding) with uncured PMMA/low temperature initiator. A secondary coating of the uncured PMMA maybe necessary to assure uniform coating of the pellet. Ideally the PMMA thickness is 0.5 mm. To form multiple layers, the same insertion molding technique is applied as described above.

When the last layer of high density polymer is to be applied, a titanium pellet is used as the mold. The pellet is placed inside of the titanium pellet with uncured PMMA. The lid to the pellet is secured and the pellet is placed into a forced air oven at about 35 degrees C. for about 6 hours to about 8 hours. The lid of the pellet has a 22 gauge opening to allow for release of the neurotoxin. In this example the pellet effectiveness can be for about 10 months to about 24 months.

Example 5

Neurotoxin Implant with Layered Column

In order to sustain release for prolonged periods of time an alternative approach is to place a layers of the high density polymer/low density polymer w/neurotoxin inside of the titanium pellet described above. Curing can be carried out in a forced air oven at about 35 degrees C. for between about 6 hours and about 8 hours for each layer applied. The diameter of the pellet would be key determinant on the amount of neurotoxin applied. The number of layers can determine how long the implant will sustain effectiveness. For each layer the thickness of the PMMA layer can be about 0.5 mm and the low density polymer w/neurotoxin can be about 0.3 mm. For each layer added, an approximately 3-month increase in effectiveness is obtained. An implant with a 2 year life can be made by increasing the length of the implant to about 6.4 mm plus the size of the titanium shell cross section about 1 mm for a total of about 7.4 mm.

Compositions and methods according to the invention disclosed herein has many advantages, including the following:

1. a single implant can be used to provide therapeutically effective continuous or pulsatile administration of a neurotoxin over a period of one year or longer.
2. the neurotoxin is delivered to a localized tissue area without a significant amount of neurotoxin appearing systemically.
3. reduced need for patient follow up care.
4. reduced need for periodic injections of neurotoxin to treat a condition, such as a neuromuscular disorder.
5. increased patent comfort due to the reduced number of injections required.
6. improved patient compliance.

An advantage of our controlled release formulations for neurotoxins include long term, consistent therapeutic levels of neurotoxin at the target tissue. The advantages also include increased patient compliance and acceptance by reducing the required number of injections.

All references, articles, publications and patents and patent applications cited herein are incorporated by reference in their entireties.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local (i.e. intramuscular, intraglandular, subcutaneous, and intracranial) administration methods wherein two or more neurotoxins, such as two or more botulinum toxins, are administered concurrently or consecutively via implant. For example, botulinum toxin type A can be administered via implant until a loss of clinical response or neutralizing antibodies develop, followed by administration via implant of a botulinum toxin type B or E. Alternately, a combination of any two or more of the botulinum serotypes A-G can be locally administered to control the onset and duration of the desired therapeutic result. Furthermore, non-neurotoxin compounds can be administered prior to, concurrently with or subsequent to administration of the neurotoxin via implant so as to provide an adjunct effect such as enhanced or a more rapid onset of denervation before the neurotoxin, such as a botulinum toxin, begins to exert its therapeutic effect.

Our invention also includes within its scope the use of a neurotoxin, such as a botulinum toxin, in the preparation of a medicament, such as a controlled release implant, for the treatment of a movement disorder, and/or a disorder influenced by cholinergic innervation, by local administration via the implant of the neurotoxin.

Accordingly, the spirit and scope of the following claims should not be limited to the descriptions of the preferred embodiments set forth above.

We claim:

1. A controlled release system, comprising:
   (a) a polymeric matrix, and;
   (b) a quantity of neurotoxin located within the polymeric matrix, wherein fractional amounts of the neurotoxin can be released from the polymeric matrix over a prolonged period of time without a significant immune system response.

2. The controlled release system of claim 1, wherein neurotoxin is released from the polymeric matrix in a continuous or monophasic manner.

3. The controlled release system of claim 1, wherein the prolonged period of time during which neurotoxin is released from the polymeric matrix extends over of a period of time of from about 10 days to about 6 years.

4. The controlled release system of claim 1, wherein the polymeric matrix is comprised of a substance which is non-biodegradable.

5. The controlled release system of claim 1, wherein the neurotoxin comprises a polypeptide.

6. The controlled release system of claim 1, wherein the neurotoxin comprises a presynaptic neurotoxin.

7. The controlled release system of claim 1, wherein the neurotoxin is a Clostridial neurotoxin.

8. The controlled release system of claim 1, wherein the neurotoxin is a botulinum toxin.

9. The controlled release system of claim 1, wherein the neurotoxin is a botulinum toxin selected from the group consisting of botulinum toxin types A, B, $C_1$, D, E, F and G.

10. The controlled release system of claim 1, wherein the neurotoxin is a botulinum toxin type A.

11. The controlled release system of claim 1, wherein the polymer which comprises the polymeric matrix is selected from the group consisting of methacrylate, vinyl pyrrolidone, vinyl alcohol, acrylic acid, polymethylmethacrylate, siloxane, vinyl acetate, lactic acid, glycolic acid, collagen, and bioceramic polymers and copolymers thereof.

12. The controlled release system of claim 1, wherein the quantity of the neurotoxin is between about 1 unit and about 50,000 units of a botulinum toxin.

13. The controlled release system of claim 1, wherein the quantity of the neurotoxin is between about 10 units and about 2,000 units of a botulinum toxin type A.

14. The controlled release system of claim 1, wherein the quantity of the neurotoxin is between about 100 units and about 30,000 units of a botulinum toxin type B.

15. The controlled release system of claim 1 wherein the neurotoxin is a botulinum toxin which is released in an amount effective to cause flaccid muscular paralysis of a muscle or muscle group at or in the vicinity of the implanted system.

16. A controlled release system, comprising:
   (a) a polymeric matrix, and;
   (b) between about 10 units and about 20,000 units of a botulinum toxin within the polymeric matrix, wherein fractional amounts of the botulinum toxin can be released from the polymeric matrix over a prolonged period of time extending from about 2 months to about 5 years without a significant immune system response.

17. A method for making a controlled release system which will not induce a significant immune response, the method comprising the steps of:
   (a) dissolving a polymer in a solvent to form a polymer solution;
   (b) mixing or dispersing a neurotoxin in the polymer solution to form a polymer-neurotoxin mixture, and;
   (c) allowing the polymer-neurotoxin mixture to set or cure, thereby making a controlled release system.

18. The method of claim 17, further comprising the step after the mixing step of evaporating solvent.

19. A method for using a continuous system release system, the method comprising injection or implantation of a controlled release system which includes a polymeric matrix and a neurotoxin, thereby treating a movement disorder or a disorder influenced by cholinergic innervation without causing a significant immune system response.

20. A method for making a metal cation-complexed neurotoxin comprising the steps of:
   (a) forming a solution containing a neurotoxin;
   (b) mixing a multivalent metal cation component with the neurotoxin solution to complex the multivalent metal cation with the neurotoxin, thereby forming a metal cation-complexed neurotoxin suspension, and;
   (c) drying said suspension to form the metal cation-complexed neurotoxin.

* * * * *